US012665056B2

(12) United States Patent
Chen et al.

(10) Patent No.: US 12,665,056 B2
(45) Date of Patent: Jun. 23, 2026

(54) METHOD AND APPARATUS FOR TRAINING MODEL, METHOD AND APPARATUS FOR GENERATING MOLECULES

(71) Applicant: Beijing Baidu Netcom Science Technology Co., Ltd., Beijing (CN)

(72) Inventors: Zhiyuan Chen, Beijing (CN); Xiaomin Fang, Beijing (CN); Fan Wang, Beijing (CN); Jingzhou He, Beijing (CN)

(73) Assignee: BEIJING BAIDU NETCOM SCIENCE TECHNOLOGY CO., LTD., Beijing (CN)

( * ) Notice: Subject to any disclaimer, the term of this patent is extended or adjusted under 35 U.S.C. 154(b) by 791 days.

(21) Appl. No.: 18/064,812

(22) Filed: Dec. 12, 2022

(65) Prior Publication Data

US 2023/0115984 A1 Apr. 13, 2023

(30) Foreign Application Priority Data

May 18, 2022 (CN) .......................... 202210544331.6

(51) Int. Cl.
*G16C 20/70* (2019.01)
*G16C 20/30* (2019.01)
*G16C 20/50* (2019.01)

(52) U.S. Cl.
CPC ............. *G16C 20/70* (2019.02); *G16C 20/30* (2019.02); *G16C 20/50* (2019.02)

(58) Field of Classification Search
None
See application file for complete search history.

(56) References Cited

U.S. PATENT DOCUMENTS

2020/0168302 A1 5/2020 Isayev et al.

FOREIGN PATENT DOCUMENTS

| CN | 111370074 A | 7/2020 |
| CN | 111695702 A | 9/2020 |
| CN | 112270951 A | 1/2021 |
| CN | 112634992 A | 4/2021 |

(Continued)

OTHER PUBLICATIONS

English machine translation of Xu et al. (CN 111695702 A) (Year: 2020).*

(Continued)

*Primary Examiner* — Walter L Lindsay, Jr.
*Assistant Examiner* — Geoffrey T Evans
(74) *Attorney, Agent, or Firm* — Seed Intellectual Property Law Group LLP

(57) ABSTRACT

The present disclosure provides a method for training a model, a method and an apparatus for generating molecules, and relates to the technical field of computer technology, particularly the technical field of artificial intelligence. The particular implementation may include: obtaining first molecular samples and second molecular samples; determining molecular difference information based on the first molecular samples and the second molecular samples; training an initial encoding module and an initial generation module based on the molecular difference information to obtain a target encoding module and a target generation module; and determining a molecule generation model based on the target encoding module and the target generation module.

12 Claims, 5 Drawing Sheets

200

(56) References Cited

FOREIGN PATENT DOCUMENTS

| | | | |
|---|---|---|---|
| CN | 112786108 | A | 5/2021 |
| CN | 114220491 | A | 3/2022 |
| JP | 2018-70692 | A | 5/2018 |
| WO | 2022/047677 | A1 | 3/2022 |

OTHER PUBLICATIONS

Bagal et al., "MolGPT: Molecular generation using a transformer-decoder model," Journal of Chemical Information and Modeling, 2021, 5 pages.

Imrie et al., "Generating property-matched decoy molecules using deep learning," Bioinformatics, 2021, 5 pages.

Jin et al., "Multi-Objective molecule generation using interpretable substructures," 37th International Conference on Machine Learning, 2020, 11 pages.

Tao, "Motif-based semi-supervised molecular autoencoder and prediction of molecular properties," with English abstract, Harbin Institute of Technology, Jun. 2021, 6 pages.

Zhang, "Study of biological network mining based function information in complex disease," with English abstract, Wuhan University, Apr. 2017, 15 pages.

* cited by examiner

<u>200</u>

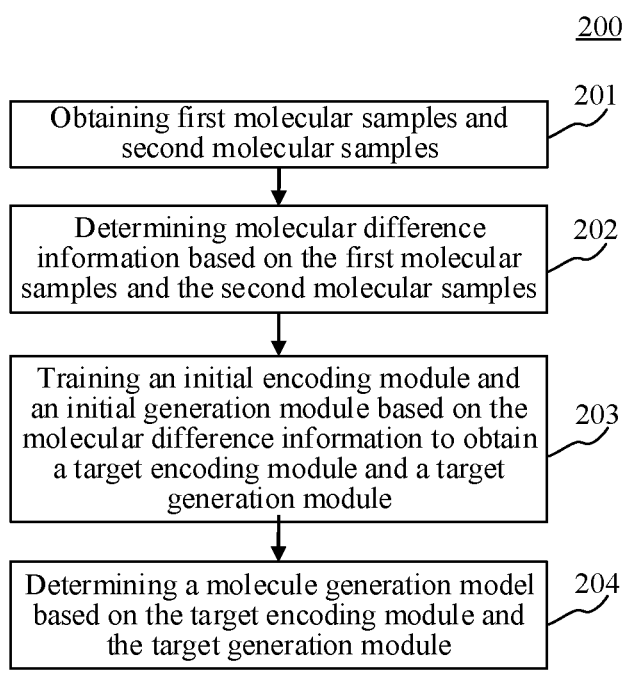

| Obtaining first molecular samples and second molecular samples | 201 |

| Determining molecular difference information based on the first molecular samples and the second molecular samples | 202 |

| Training an initial encoding module and an initial generation module based on the molecular difference information to obtain a target encoding module and a target generation module | 203 |

| Determining a molecule generation model based on the target encoding module and the target generation module | 204 |

Fig. 2

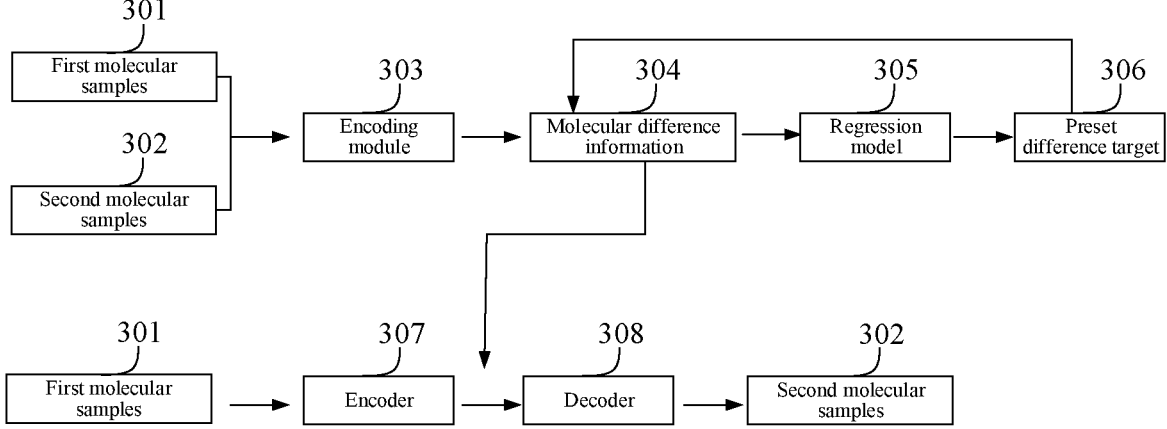

Fig. 3

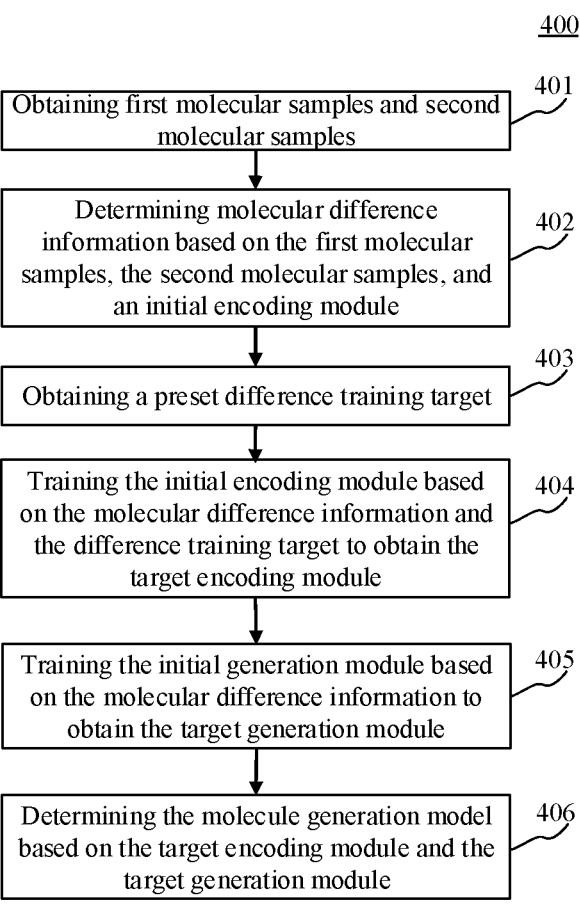

400

Obtaining first molecular samples and second molecular samples    401

Determining molecular difference information based on the first molecular samples, the second molecular samples, and an initial encoding module    402

Obtaining a preset difference training target    403

Training the initial encoding module based on the molecular difference information and the difference training target to obtain the target encoding module    404

Training the initial generation module based on the molecular difference information to obtain the target generation module    405

Determining the molecule generation model based on the target encoding module and the target generation module    406

Fig. 4

METHOD AND APPARATUS FOR TRAINING MODEL, METHOD AND APPARATUS FOR GENERATING MOLECULES

CROSS-REFERENCE TO RELATED APPLICATIONS

The present application claims the priority of Chinese Patent Application No. 202210544331.6, titled "METHOD AND APPARATUS FOR TRAINING MODEL, METHOD AND APPARATUS FOR GENERATING MOLECULES" filed on May 18, 2022, the content of which is incorporated herein by reference in its entirety.

TECHNICAL FIELD

The present disclosure relates to the field of computer technology, and in particular to the field of artificial intelligence.

BACKGROUND

Currently, in a scenario of drug design, it is necessary to identify molecules with specific properties from a large chemical space.

In this regard, the molecules with specific properties are now often determined based on a virtual screening technique.

SUMMARY

The present disclosure provides a method and an apparatus for training a model, and also provides a method and an apparatus for generating molecules.

In a first aspect, embodiments of the present disclosure provide a method for training a model, comprising: obtaining first molecular samples and second molecular samples; determining molecular difference information based on the first molecular samples and the second molecular samples; training an initial encoding module and an initial generation module based on the molecular difference information to obtain a target encoding module and a target generation module; and determining a molecule generation model based on the target encoding module and the target generation module.

In a second aspect, embodiments of the present disclosure provide a method for generating molecules, comprising: obtaining to-be-optimized molecules; determining an optimizing target of the to-be-optimized molecules; and generating optimized molecules corresponding to the to-be-optimized molecules based on the to-be-optimized molecules, the optimizing target, and the molecule generation model obtained by performing the method described above for training the model.

In a third aspect, embodiments of the present disclosure provide an apparatus for training a model, comprising: a sample acquisition unit, configured to obtain first molecular samples and second molecular samples; a difference determination unit, configured to determine molecular difference information based on the first molecular samples and the second molecular samples; a module training unit, configured to train an initial encoding module and an initial generation module based on the molecular difference information to obtain a target encoding module and a target generation module; and a model determination unit, configured to determine a molecule generation model based on the target encoding module and the target generation module.

In a fourth aspect, embodiments of the present disclosure provide an apparatus for generating molecules, comprising: a molecule acquisition unit, configured to obtain to-be-optimized molecules; a target determining unit, configured to determine an optimizing target of the to-be-optimized molecules; and a molecule generation unit, configured to generate optimized molecules corresponding to the to-be-optimized molecules based on the to-be-optimized molecules, the optimizing target, and the molecule generation model obtained by performing the method described above for training the model.

In a fifth aspect, embodiments of the present disclosure provide an electronic device, comprising: one or more processors; and a memory, storing one or more programs, wherein the one or more programs, when executed by the one or more processors, cause the one or more processors to implement the method provided by the first aspect or the second aspect.

In a sixth aspect, embodiments of the present disclosure provide a computer-readable medium, storing a computer program thereon, wherein the program, when executed by a processor, causes the processor to implement the method provided by the first aspect or the second aspect.

In a seventh aspect, an embodiment of the present disclosure provides a computer program product, comprising a computer program, wherein the computer program, when executed by a processor, implements the method provided by the first aspect or the second aspect.

It should be understood that contents described in this section are neither intended to identify key or important features of embodiments of the present disclosure, nor intended to limit the scope of the present disclosure. Other features of the present disclosure will become readily understood in conjunction with the following description.

BRIEF DESCRIPTION OF THE DRAWINGS

The accompanying drawings are used for better understanding of the present solution, and do not constitute a limitation to the present disclosure. In which:

FIG. 2 is a flowchart of a method for training a model according to an embodiment of the present disclosure;

FIG. 3 is a schematic diagram of an application scenario of a method for training a model according to the present disclosure;

FIG. 4 is a flowchart of a method for training the model according to another embodiment of the present disclosure;

DETAILED DESCRIPTION OF EMBODIMENTS

Example embodiments of the present disclosure are described below with reference to the accompanying drawings, where various details of the embodiments of the present disclosure are included to facilitate understanding, and should be considered merely as examples. Therefore, those of ordinary skills in the art should realize that various changes and modifications can be made to the embodiments described here without departing from the scope and spirit of the present disclosure. Similarly, for clearness and conciseness, descriptions of well-known functions and structures are omitted in the following description.

It is noted that the embodiments in the present disclosure and the features in the embodiments may be combined with each other without conflict. The present disclosure will now be described in detail with reference to the accompanying drawings and examples.

Figure 1:
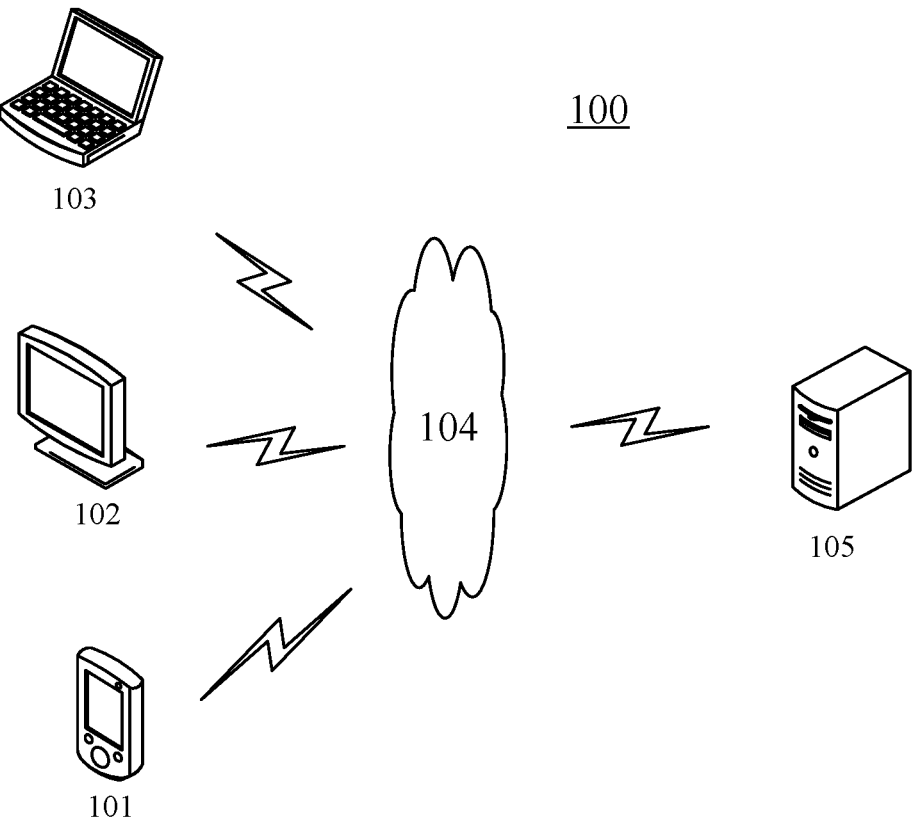
FIG. 1 is an exemplary system architecture in which an embodiment of the present disclosure may be applied.

As shown in FIG. 1, the system architecture 100 may include terminal devices 101, 102, 103, a network 104, and a server 105. The network 104 serves as a medium for providing a communication link between the terminal devices 101, 102, 103 and the server 105. N The network 104 may include various types of connections, such as wired, wire smaller communication links, or fiber optic cables, among others.

The user may interact with the server 105 through the network 104 using the terminal devices 101, 102, 103 to receive or send messages, etc. The terminal devices 101, 102, 103 may obtain first molecular samples and second molecular samples, and send the first molecular samples and the second molecular samples to the server 105 through the network 104 so that the server 105 can train to obtain a molecular generation model based on the first molecular samples and the second molecular samples as training samples. Thereafter, the terminal devices 101, 102, and 103 may obtain the molecular generation model, and determine optimized molecules corresponding to the to-be-optimized molecules based on the molecular generation model.

The terminal devices 101, 102, 103 may be hardware or software. When the terminal devices 101, 102, 103 are hardware, various electronic devices may be used, including but not limited to a mobile phone, a computer, a tablet, and the like. When the terminal devices 101, 102, and 103 are software, they may be installed in the electronic devices listed above. It may be implemented as a plurality of software or software modules (e.g., for providing distributed services) or as a single software or software module. It is not specifically limited herein.

The server 105 may be a server providing various services, for example, the server 105 may receive the first molecular samples and the second molecular samples sent by the terminal devices 101, 102, 103 over the network 104, and determine molecular difference information based on the first molecular samples and the second molecular samples. And training the initial encoding module and the initial generation module based on the molecular difference information to obtain the target encoding module and the target generation module. And determining a molecular generation model based on the target encoding module and the target generation module. Thereafter, the server 105 may transmit the molecular generation model to the terminal devices 101, 102, 103 through the network 104 so that the terminal devices 101, 102, 103 generate optimized molecules of the to-be-optimized molecules through the molecular generation model.

It should be noted that the server 105 may be hardware or software. When the server 105 is hardware, it may be implemented as a distributed server cluster of multiple servers, or it may be implemented as a single server. When the server 105 is software, it may be implemented as a plurality of software or software modules (e.g., for providing distributed services), or it may be implemented as a single software or software module. It is not specifically limited herein.

It should be noted that the method for training the model or the method for generating the molecules provided in the embodiment of the present disclosure may be performed by the terminal devices 101, 102, and 103, or may be performed by the server 105. The device for training the model or the device for generating the molecules may be provided in the terminal devices 101, 102, and 103, or may be provided in the server 105, which is not limited in the embodiment of the present disclosure.

It should be understood that the number of the terminal devices, the networks and the servers in FIG. 1 is merely illustrative. There may be any number of the terminal devices, the networks and the servers as desired for implementation.

Further referring to FIG. 2, FIG. 2 illustrates a flow 200 of a method for training a model according to an embodiment of the present disclosure. The method for training the model of the present embodiment includes the steps 201-204.

Step 201: obtaining first molecular samples and second molecular samples.

In the present embodiment, an execution body (such as the server 105 or the terminal devices 101, 102, 103 in FIG. 1) may obtain first molecular samples and second molecular samples from a locally stored or pre-connected electronic device. The number of the first molecular samples or the second molecular samples may be at least one, and a first molecular sample and a second molecular sample corresponding to the first molecular sample may constitute a group of molecular samples having a corresponding relationship.

The first molecular samples may be to-be-optimized molecular samples, and the second molecular samples may be to-be-optimized molecular samples corresponding to the first molecular samples. A molecule refers to an entirety composed of atoms bonded together in a certain bonding order and spatial arrangement.

Step 202: determining molecular difference information based on the first molecular samples and the second molecular samples.

In this embodiment, the execution body may input the first molecular samples and the second molecular samples to an initial encoding module to obtain the molecular difference information output by the initial encoding module. Alternatively, the execution body may analyze molecular properties of the first molecular samples and the second molecular samples to obtain the molecular difference information. The molecular difference information may be used to describe a difference in molecular properties between the first molecular samples and the second molecular samples, for example, the molecular difference information may have a specific molecular property, such as having a lipophilic property, having a hydrophilic property, having an affinity to a target, and the like, which is not limited in this embodiment. Preferably, the molecular difference information may be a vector.

In step 203, training an initial encoding module and an initial generation module based on the molecular difference information to obtain a target encoding module and a target generation module.

In the present embodiment, an initial encoding module may be used to determine an optimal molecular difference information, and the initial generation module may be used to generate second molecular samples based on the first molecular samples and the optimal molecular difference information. The initial encoding module may employ an Multilayer Perceptron (MLP), an Encoder module in a Transformer model (a model that utilizes an attention mechanism to improve a training speed of a model), or the like. The initial generation module may employ various models conforming to an Encoder-Decoder architecture, such as the Transformer model. For example, the initial generation module may include an Encoder module and a Decoder module in the Transformer model.

Further, after obtaining the molecular difference information between the first molecular samples and the second molecular samples, the execution body may perform parallel training on the initial encoding module and the initial generation module based on the molecular difference information. The execution body may perform asynchronous training on the initial encoding module and the initial generation module based on the molecular difference information. Preferably, the initial encoding module and the initial generation module are trained by parallel training to obtain the target encoding module and the target generation module. A module training efficiency can be improved by means of parallel training, and a mutual influence between the initial encoding module and the initial generation module can be considered in a training process, such that an accuracy of a module training is improved.

In some alternative implementations of the present embodiment, the training the initial encoding module and the initial generation module based on the molecular difference information to obtain the target encoding module and the target generation module may include: performing iterative optimization on the initial encoding module based on a preset difference target to obtain optimized molecular difference information output by an iteratively optimized initial encoding module in response to determining that the initial encoding module and the initial generation module are trained by parallel training; performing iterative optimization on the initial generation module based on the optimized molecular difference information obtained by each iterative optimization; In response to determining that a difference between the optimized molecular difference information output by the initial encoding module and the difference target satisfies a preset difference condition, determining the initial encoding module at this time as the target encoding module; in response to determining that a difference between the molecules output by the initial generation module based on the first molecule samples and the second molecule samples is smaller than a preset difference threshold, the initial generation module at this time is determined as the target generation module. Preferably, the execution body may further adjust a number of training steps for the initial generation module and a number of training steps for the initial encoding module, so as to realize synchronous parallel training and improve a training effect.

Step 204: determining a molecule generation model based on the target encoding module and the target generation module.

In this embodiment, the execution body may combine the target encoding module and the target generation module to obtain the molecule generation model. The molecule generation model can iteratively determine an optimal molecular difference information satisfying the optimizing target according to input to-be-optimized molecules and the optimizing target, and generate optimized molecules based on the optimal molecular difference information and the to-be-optimized molecules.

Further referring to FIG. 3, FIG. 3 illustrates a schematic diagram of an application scenario of a method for training a model according to the present disclosure. In the application scenario of FIG. 3, the execution body may obtain the first molecular samples 301 and the second molecular samples 302. Thereafter, the execution body may input the first molecular samples 301 and the second molecular samples 302 to the encoding module 303 to obtain the molecular difference information 304 output by the encoding module 303. Thereafter, the execution body may input the molecular difference information 304 into a regression model 305, so that the regression model 305 compares the molecular difference information 304 with the preset difference target 306 to obtain a difference evaluation result for the molecular difference information 304. In response to determining that the difference evaluation result fails to satisfy the difference condition, the encoding module 303 is iteratively optimized to obtain the molecular difference information 304 redetermined after the iterative optimization of the encoding module 303. The execution body may repeat the above steps, continue to input the molecular difference information 304 into the regression module 305, and iteratively optimize the encoding module 303 until a trained encoding module 303 is obtained. Meanwhile, in a process of training the encoding module 303, the execution body may obtain the molecular difference information 304 generated by each iteration, and train the generation module based on the molecular difference information 304. The generation module may include an encoder 307 and a decoder 308. The execution body may input the first molecular samples 301 to the encoder 307 to obtain an encoding result for the first molecular samples 301. The encoding result and the molecular difference information 304 generated by each iteration are then input to the decoder 308 to obtain molecules output by the decoder 308. The execution body may train the generation module based on a difference between the molecules output by the decoder 308 and the second molecular samples, so as to bring the molecules output by the generation module closer to the second molecular samples 302.

According to the method for training the model provided in the above embodiment of the present disclosure, the initial encoding module and the initial generation module are trained based on the molecular difference information between the first molecular samples and the second molecular samples to obtain the target encoding module and the target generation module, thereby obtaining the molecule generation model. The molecule generation model obtained by the model training method can generate molecules with specific properties based on the molecular difference information, so that the accuracy of the molecule generation can be improved.

Further referring to FIG. 4, FIG. 4 illustrates a flow 400 of a method for training the model according to another embodiment of the present disclosure. As shown in FIG. 4, the method for training the model of the present embodiment may include the following steps 401-406.

Step 401: obtaining first molecular samples and second molecular samples.

In the present embodiment, for the detailed description of the step 401, reference is made to the detailed description of the step 201, and details are not described herein.

Step 402: determining molecular difference information based on the first molecular samples, the second molecular samples, and an initial encoding module.

In the present embodiment, the execution body may input first molecular samples and second molecular samples to an initial encoding module, so that the initial encoding module encodes the first molecular samples and the second molecular samples to obtain molecular difference information.

For the detailed description of the step 402, reference is made to the detailed description of the step 202, and details are not described herein.

Step 403: obtaining a preset difference training target.

In the present embodiment, the preset difference training target may be determined according to different training requirements, for example, in a case where a training requirement is that the molecule generation model is capable of generating molecules having specific properties, the execution body may set a difference training target to have the specific properties in advance.

Step 404: training the initial encoding module based on the molecular difference information and the difference training target to obtain the target encoding module.

In this embodiment, after obtaining the molecular difference information, the execution body may compare the molecular difference information with the difference training target. When the difference between the molecular difference information and the difference training target is large, module parameters of the initial encoding module can be adjusted, so as to redetermine the molecular difference information based on the initial encoding module whose parameters have been adjusted, until the difference between a redetermined molecular difference information and the difference training target is smaller than a preset difference threshold, and the initial encoding module at this time is determined as the target encoding module.

In some alternative implementations of the present embodiment, the training the initial encoding module to obtain the target encoding module based on the molecular difference information and the difference training target may include: determining a difference evaluation result corresponding to the molecular difference information based on the molecular difference information and the difference training target; and determining the initial encoding module as the target encoding module in response to determining that the difference evaluation result satisfies a preset difference condition.

In the present implementation, the execution body may generate a corresponding difference evaluation result according to the molecular difference information and the difference training target by using an evaluation model. The evaluation model may be any differentiable regression model. The difference evaluation result may be used to describe the difference between the molecular difference information and the difference training target, and the preset difference condition may be that the difference indicated by the difference evaluation result between the molecular difference information and the difference training target is small, for example, the difference between the molecular difference information and the difference training target is smaller than the preset difference threshold.

Optionally, in a process of training the initial encoding module, it is possible to restrict the molecular difference information to obey a specific distribution, so as to facilitate model calculation. The specific distribution may be any distribution that can be easily sampled. For example, the specific distribution may be a standard normal distribution.

In other alternative implementations of the present embodiment, the method further includes: in response to determining that the difference evaluation result fails to satisfy the difference condition, iteratively adjusting parameters of the initial encoding module to update the molecular difference information until an updated difference evaluation result satisfies the difference condition.

In the present implementation, the execution body may determine that the difference between the molecular difference information and the difference training target is large in response to determining that the difference evaluation result fails to satisfy the difference condition, and the molecular difference information at this time cannot reflect a property difference between the first molecular samples and the second molecular samples well. At this time, the execution body may iteratively adjust the parameters of the initial encoding module to obtain the initial encoding module whose parameters are adjusted, and redetermine the molecular difference information based on the initial encoding module whose parameters are adjusted until the difference evaluation result corresponding to the redetermined molecular difference information satisfies the above-mentioned difference condition, thereby obtaining the target encoding module.

Step 405: training the initial generation module based on the molecular difference information to obtain the target generation module.

In the present embodiment, the execution body may send the molecular difference information to the initial generation module every time after the execution body obtains the molecular difference information in a process of training the initial encoding module, so as to train the initial generation module to obtain the target generation module. Alternatively, the execution body may first train the initial encoding module to obtain the target encoding module. After obtaining the target encoding module, the execution body sends each piece of statistical molecular difference information to the initial generation module to train the initial generation module.

In some alternative implementations of the present embodiment, the training the initial generation module based on the molecular difference information to obtain the target generation module, includes: obtaining the molecular difference information; determining updated information of the molecular difference information in a process of training the initial encoding module; determining third molecular samples output by the initial generation module based on the first molecular samples, the molecular difference information, and the updated information; and training the initial generation module based on the third molecular samples and the second molecular samples to obtain the target generation module.

In the present implementation, the execution body may first obtain the initial molecular difference information, and then, after adjusting the module parameters of the initial encoding module each time in a process of training the initial encoding module, the execution body may determine the molecular difference information redetermined by the initial encoding module whose module parameters are adjusted. The updated information may indicate the molecular difference information every time the module parameters of the initial encoding module are iteratively adjusted, and the molecular difference information after each update may be determined based on the updated information.

Also, the execution body may determine the target molecular difference information of each module training based on the molecular difference information and the updated information; then, the execution body may input the first molecular samples and the target molecular difference information to the initial generation module to obtain the third molecular samples output by the initial generation module. Thereafter, the execution body may compare the second molecular samples and the third molecular samples, and construct a loss function based on a difference between the second molecular samples and the third molecular samples, and training the initial generation module based on the loss function until the difference between the second molecular samples and the third molecular samples is smaller than a preset difference value, so as to obtain the target generation module.

Alternatively, the generation module may include an encoder and a decoder. When the first molecular samples and the target molecular difference information are input to the initial generation module, the first molecular samples may be input to the encoder so that the encoder encodes the first molecular samples to obtain an encoding result of the first molecular samples. And then, feature fusion is performed on the encoding result and the target molecular difference information, and a feature-fused molecular encoding result is input into the decoder to obtain the third molecular samples output by the decoder.

Step 406: determining the molecule generation model based on the target encoding module and the target generation module.

In the present embodiment, for the detailed description of the step 406, reference is made to the detailed description of the step 204, and details are not described herein.

According to the method for training the model provided in the above embodiment of the present invention, different difference training targets can be preset in advance to optimize the molecular difference information, so that the trained molecule generation model can adapt to the molecule generation requirements in various real scenes. And, the generation module in the molecule generation model may not provide hidden space, thereby reducing data loss caused by data compression. And, the molecular difference information may be input before the decoder, avoiding the need to encode and then decode, thereby further improving an accuracy of data.

Figure 5:
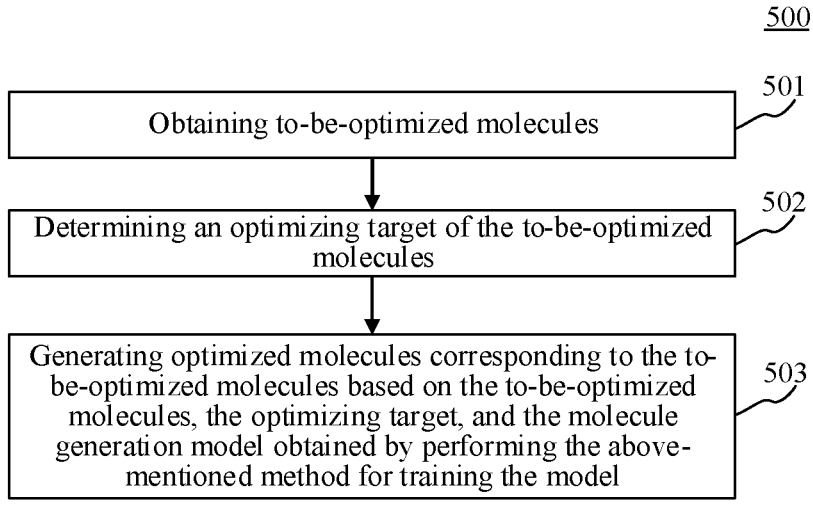
FIG. 5 is a flowchart of a method for generating molecules according to an embodiment of the present disclosure.

Further referring to FIG. 5, FIG. 5 illustrates a flow 500 of a method for generating molecules according to an embodiment of the present disclosure. The method for generating the molecules of the present embodiment includes the steps of 501-503.

Step 501: obtaining to-be-optimized molecules.

In this embodiment, the to-be-optimized molecules may be a molecular skeleton or a complete molecular structure, and which is not limited thereto.

Step 502: determining an optimizing target of the to-be-optimized molecules.

In the present embodiment, the execution body may determine the optimizing target of the to-be-optimized molecules based on the human-computer interaction with the user. The optimizing target may be to make the molecules have specific molecular properties.

Step 503: generating optimized molecules corresponding to the to-be-optimized molecules based on the to-be-optimized molecules, the optimizing target, and the molecule generation model obtained by performing the above-mentioned method for training the model.

In the embodiment, the execution body may input the to-be-optimized molecules and the optimizing target into the molecule generation model to obtain the optimized molecules output by the above molecule generation model.

In some alternative implementations of this embodiment, the generating the optimized molecules corresponding to the to-be-optimized molecules based on the to-be-optimized molecules, the optimizing target, and the molecule generation model obtained by performing the above-described method for training the model, may include: determining target molecular difference information based on the to-be-optimized molecules, the optimizing target, and a target encoding module in the molecule generation model; generating the optimized molecules based on the to-be-optimized molecules, the target molecular difference information, and the target generation module in the molecule generation model.

In the present implementation, the execution body may first randomly select the initial molecular difference information for the to-be-optimized molecules from the molecular difference information satisfying a specific distribution through the target encoding module. Then, based on the difference between the initial molecular difference information and the optimizing target, the initial molecular difference information is iteratively adjusted to obtain the target molecular difference information, and the target molecular difference information is used as an optimal molecular difference information. Then, the optimized molecules are generated by the target generation module based on the to-be-optimized molecules and the optimal molecular difference information.

In other alternative implementations of the present embodiment, the determining the target molecular difference information based on the to-be-optimized molecules, the optimizing target, and the target encoding module in the molecule generation model includes: determining initial molecular difference information corresponding to the to-be-optimized molecules based on the target encoding module; and iteratively adjusting the initial molecular difference information based on the optimizing target to obtain the target molecular difference information.

In the present implementation, the execution body may input the to-be-optimized molecules into the target encoding module to obtain the initial molecular difference information output by the target encoding module. Thereafter, the execution body may input the initial molecular difference information into an evaluation model, so that the evaluation model determines a difference evaluation result corresponding to the initial molecular difference information based on difference between the optimizing target and the initial molecular difference information. Then, the execution body may iteratively adjust the initial molecular difference information based on the difference evaluation result until the difference evaluation result corresponding to the adjusted initial molecular difference information satisfies the preset difference condition, and determine the initial molecular difference information at this time as the target molecular difference information.

According to the method for generating the molecules provided in the above embodiments of the present disclosure, the optimized molecules corresponding to the to-be-optimized molecules can be generated by using the above-described molecule generation model, so that the generated optimized molecules have specific properties, thereby improving the accuracy of the molecule generation.

Figure 6:
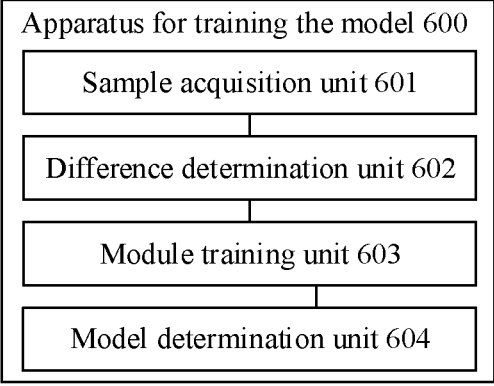
FIG. 6 is a schematic structural diagram of an apparatus for training a model according to an embodiment of the present disclosure.

Further referring to FIG. 6, as an implementation of the method shown in each of the above figures, the present disclosure provides an embodiment of an apparatus for training a model, which corresponds to the method embodiment shown in FIG. 6, and is particularly applicable to electronic devices such as terminal devices and servers.

As shown in FIG. 6, the apparatus 600 for training the model provided in the present embodiment includes a sample acquisition unit 601, a difference determination unit 602, a module training unit 603, and a model determination unit 604.

The sample acquisition unit 601 is configured to obtain first molecular samples and second molecular samples.

The difference determination unit 602 is configured to determine molecular difference information based on the first molecular samples and the second molecular samples.

The module training unit 603 is configured to train an initial encoding module and an initial generation module based on the molecular difference information to obtain a target encoding module and a target generation module.

The model determination unit 604 is configured to determine a molecule generation model based on the target encoding module and the target generation module.

In some alternative implementations of the present embodiment, the module training unit 603 is further configured to obtain a preset difference training target, train the initial encoding module to obtain the target encoding module based on the molecular difference information and the difference training target, and train the initial generation module based on the molecular difference information to obtain the target generation module.

In some alternative implementations of the present embodiment, the module training unit 603 is further configured to determine a difference evaluation result corresponding to the molecular difference information based on the molecular difference information and the difference training target; and determine the initial encoding module as the target encoding module in response to determining that the difference evaluation result satisfies the preset difference condition.

In some alternative implementations of the present embodiment, the module training unit 603 is further configured to in response to determining that the difference evaluation result fails to satisfy the difference condition, iteratively adjust parameters of the initial encoding module to update the molecular difference information until an updated difference evaluation result satisfies the difference condition.

In some alternative implementations of the present embodiment, the difference determination unit 602 is further configured to determine molecular difference information based on the first molecular samples, the second molecular samples, and the initial encoding module.

It should be understood that the units 601 to 604 described in the apparatus 600 for training the model correspond to the respective steps in the method described in FIG. 2. Thus, the operations and features described above with respect to the method for training the model are equally applicable to the apparatus 600 and the units contained therein, and will not be further described herein.

Figure 7:
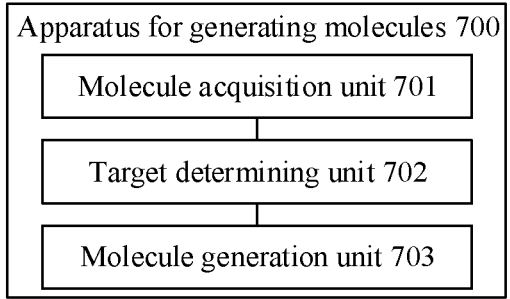
FIG. 7 is a schematic structural diagram of an apparatus for generating molecules according to an embodiment of the present disclosure.

Further referring to FIG. 7, as an implementation of the method shown in each of the above figures, the present disclosure provides an embodiment of an apparatus for generating the molecules, which corresponds to the method embodiment shown in FIG. 5, and is particularly applicable to electronic devices such as terminal devices and servers.

As shown in FIG. 7, the apparatus 700 for generating molecules according to the present embodiment includes a molecule acquisition unit 701, a target determining unit 702, and a molecule generation unit 703.

The molecule acquisition unit 701 is configured to obtain to-be-optimized molecules.

The target determining unit 702 is configured to determine an optimizing target of the to-be-optimized molecules.

The molecule generating unit 703 is configured to generate optimized molecules corresponding to the to-be-optimized molecules based on the to-be-optimized molecules, the optimizing target, and the molecule generation model obtained by performing the above-mentioned method for training the model.

In some alternative implementations of the present embodiment, the molecule generation unit 703 is further configured to determine target molecular difference information based on the to-be-optimized molecules, the optimizing target, and a target encoding module in the molecule generation model; generate the optimized molecules based on the to-be-optimized molecules, the target molecular difference information, and the target generation module in the molecule generation model.

In some alternative implementations of the present embodiment, the molecule generating unit 703 is further configured to determine initial molecular difference information corresponding to the to-be-optimized molecules based on the target encoding module; and iteratively adjust the initial molecular difference information based on the optimizing target to obtain the target molecular difference information.

It should be understood that the units 701 to 703 described in the apparatus 700 for generating the molecules correspond to the respective steps in the method described in FIG. 5. Thus, the operations and features described above with respect to the method for generating the molecules are equally applicable to the apparatus 700 and the units contained therein, and are not described herein again.

According to an embodiment of the present disclosure, the present disclosure also provides an electronic device, a readable storage medium, and a computer program product.

Figure 8:
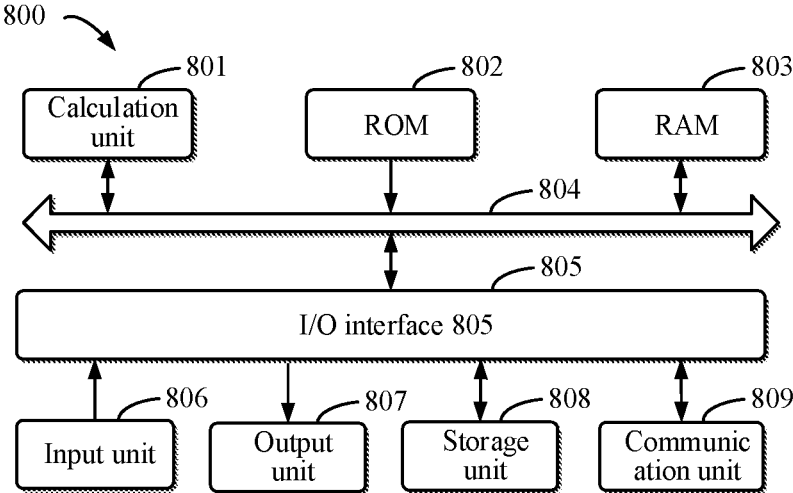
FIG. 8 is a block diagram of an electronic device used to implement a method for training a model or a method for generating molecules according to an embodiment of the present disclosure.

FIG. 8 illustrates a schematic block diagram of an example electronic device 800 that may be used to implement embodiments of the present disclosure. The electronic device is intended to represent various forms of digital computers, such as laptop computers, desktop computers, worktables, personal digital assistants, servers, blade servers, mainframe computers, and other suitable computers. The electronic device may also represent various forms of mobile devices, such as personal digital processing, cellular telephones, smart phones, wearable devices, and other similar computing devices. The components shown herein, their connections and relationships, and their functions are by way of example only and are not intended to limit the implementation of the disclosure described and/or claimed herein.

As shown in FIG. 8, The electronic device 800 includes a calculation unit 801, which may perform various appropriate actions and processes according to a computer program stored in a read-only memory (ROM) 802 or a computer program loaded into a random access memory (RAM) 803 from a storage unit 808. In RAM 803, various programs and data required for operation of the device 800 may also be stored. The calculation units 801, ROM 802 and RAM 803 are connected to each other via a bus 804. An input/output (I/O) interface 805 is also connected to bus 804.

A plurality of components in the device 800 are connected to the I/O interface 805, including: an input unit 806, such as a keyboard, a mouse, and the like; an output unit 807, such as, various types of displays, speakers, and the like; a storage unit 808, such as a magnetic disk, an optical disk, or the like; and a communication unit 809, such as a network card, a modem, or a wire smaller communication transceiver. The communication unit 809 allows the device 800 to exchange information/data with other devices over a computer network such as the Internet and/or various telecommunications networks.

The calculation unit 801 may be various general-purpose and/or special-purpose processing components having processing and computing capabilities. Some examples of calculation units 801 include, but are not limited to, central processing units (CPUs), graphics processing units (GPUs), various specialized artificial intelligence (AI) computing chips, various computing units that run machine learning model algorithms, digital signal processors (DSPs), and any suitable processors, controllers, microcontrollers, and the like. The calculation unit 801 performs various methods and processes described above, such as a method for training a model or a method for generating molecules. For example, in some embodiments, a method for training the model or a method for generating the molecules may be implemented as a computer software program tangibly embodied in a machine-readable medium, such as a storage unit 808. In some embodiments, some or all of the computer program may be loaded and/or installed on the device 800 via the ROM 802 and/or the communication unit 809. When the computer program is loaded into the RAM 803 and executed by the calculation unit 801, one or more steps of the method for training the model or the method for generating the molecules described above may be performed. Alternatively, in other embodiments, the calculation unit 801 may be configured to perform a method for training the model or a method for generating the molecules by any other suitable means (e.g., by means of firmware).

According to the technology of the present disclosure, the method for training the model or the method for generating the molecules is provided, which can improve a precision of molecule generation.

Various implementations of the systems and technologies described above herein may be implemented in a digital electronic circuit system, an integrated circuit system, a field programmable gate array (FPGA), an application specific integrated circuit (ASIC), an application specific standard product (ASSP), a system on chip (SOC), a complex programmable logic device (CPLD), computer hardware, firmware, software, and/or a combination thereof. The various implementations may include: an implementation in one or more computer programs that are executable and/or interpretable on a programmable system including at least one programmable processor, which may be a special-purpose or general-purpose programmable processor, and may receive data and instructions from, and transmit data and instructions to, a storage system, at least one input apparatus, and at least one output device.

Program codes for implementing the method of the present disclosure may be compiled using any combination of one or more programming languages. The program codes may be provided to a processor or controller of a general-purpose computer, a special-purpose computer, or other programmable apparatuses for training a model, such that the program codes, when executed by the processor or controller, cause the functions/operations specified in the flow charts and/or block diagrams to be implemented. The program codes may be completely executed on a machine, partially executed on a machine, executed as a separate software package on a machine and partially executed on a remote machine, or completely executed on a remote machine or server.

In the context of the present disclosure, the machine-readable medium may be a tangible medium which may contain or store a program for use by, or used in combination with, an instruction execution system, apparatus or device. The machine-readable medium may be a machine-readable signal medium or a machine-readable storage medium. The machine-readable medium may include, but is not limited to, electronic, magnetic, optical, electromagnetic, infrared, or semiconductor systems, apparatuses, or devices, or any appropriate combination of the above. A more specific example of the machine-readable storage medium will include an electrical connection based on one or more pieces of wire, a portable computer disk, a hard disk, a random-access memory (RAM), a read-only memory (ROM), an erasable programmable read-only memory (EPROM or flash memory), an optical fiber, a portable compact disk read-only memory (CD-ROM), an optical storage device, an optical storage device, a magnetic storage device, or any appropriate combination of the above.

To provide interaction with a user, the systems and technologies described herein may be implemented on a computer that is provided with: a display apparatus (e.g., a CRT (cathode ray tube) or a LCD (liquid crystal display) monitor) configured to display information to the user; and a keyboard and a pointing apparatus (e.g., a mouse or a trackball) by which the user can provide an input to the computer. Other kinds of apparatuses may also be configured to provide interaction with the user. For example, feedback provided to the user may be any form of sensory feedback (e.g., visual feedback, auditory feedback, or haptic feedback); and an input may be received from the user in any form (including an acoustic input, a voice input, or a tactile input).

The systems and technologies described herein may be implemented in a computing system (e.g., as a data server) that includes a back-end component, or a computing system (e.g., an application server) that includes a middleware component, or a computing system (e.g., a user computer with a graphical user interface or a web browser through which the user can interact with an implementation of the systems and technologies described herein) that includes a front-end component, or a computing system that includes any combination of such a back-end component, such a middleware component, or such a front-end component. The components of the system may be interconnected by digital data communication (e.g., a communication network) in any form or medium. Examples of the communication network include: a local area network (LAN), a wide area network (WAN), and the Internet.

The computer system may include a client and a server. The client and the server are generally remote from each other, and usually interact via a communication network. The relationship between the client and the server arises by virtue of computer programs that run on corresponding computers and have a client-server relationship with each other. The server may be a cloud server, a distributed system server, or a server combined with a blockchain.

It should be understood that the various forms of processes shown above may be used to reorder, add, or delete steps. For example, the steps disclosed in the present disclosure may be executed in parallel, sequentially, or in different orders, as long as the desired results of the technical solutions disclosed in the present disclosure can be implemented. This is not limited herein.

The above specific implementations do not constitute any limitation to the scope of protection of the present disclosure. It should be understood by those skilled in the art that various modifications, combinations, sub-combinations, and replacements may be made according to the design requirements and other factors. Any modification, equivalent replacement, improvement, and the like made within the spirit and principle of the present disclosure should be encompassed within the scope of protection of the present disclosure.

What is claimed is:

1. A method for training a model, comprising:

obtaining first molecular samples and second molecular samples;

determining molecular difference information based on the first molecular samples and the second molecular samples;

training an initial encoding module and an initial generation module based on the molecular difference information to obtain a target encoding module and a target generation module; and determining a molecule generation model based on the target encoding module and the target generation module, wherein the training an initial encoding module and an initial generation module based on the molecular difference information to obtain a target encoding module and a target generation module, comprises:

obtaining a preset difference training target;

training the initial encoding module based on the molecular difference information and the difference training target to obtain the target encoding module; and training the initial generation module based on the molecular difference information to obtain the target generation module.

2. The method of claim 1, wherein the training the initial encoding module based on the molecular difference information and the difference training target to obtain the target encoding module, comprises:

determining a difference evaluation result corresponding to the molecular difference information based on the molecular difference information and the difference training target; and determining the initial encoding module as the target encoding module in response to determining that the difference evaluation result satisfies a preset difference condition.

3. The method of claim 2, further comprising:

in response to determining that the difference evaluation result fails to satisfy the difference condition, iteratively adjusting parameters of the initial encoding module to update the molecular difference information until an updated difference evaluation result satisfies the difference condition.

4. The method of claim 1, wherein the training the initial generation module based on the molecular difference information to obtain the target generation module, comprises:

obtaining the molecular difference information;

determining updated information of the molecular difference information in a process of training the initial encoding module;

determining third molecular samples output by the initial generation module based on the first molecular samples, the molecular difference information, and the updated information; and training the initial generation module based on the third molecular samples and the second molecular samples to obtain the target generation module.

5. The method of claim 1, wherein the determining molecular difference information based on the first molecular samples and the second molecular samples, comprises:

determining the molecular difference information based on the first molecular samples, the second molecular samples, and the initial encoding module.

6. A method for generating molecules, comprising:

obtaining to-be-optimized molecules;

determining an optimizing target of the to-be-optimized molecules; and generating optimized molecules corresponding to the to-be-optimized molecules based on the to-be-optimized molecules, the optimizing target, and the molecule generation model obtained by performing operations for training a model, the operations comprising:

obtaining first molecular samples and second molecular samples;

determining molecular difference information based on the first molecular samples and the second molecular samples;

training an initial encoding module and an initial generation module based on the molecular difference information to obtain a target encoding module and a target generation module; and determining a molecule generation model based on the target encoding module and the target generation module, wherein the generating optimized molecules corresponding to the to-be-optimized molecules based on the to-be-optimized molecules, the optimizing target, and the molecule generation model, comprises:

determining target molecular difference information based on the to-be-optimized molecules, the optimizing target, and a target encoding module in the molecule generation model; and generating the optimized molecules based on the to-be-optimized molecules, the target molecular difference information, and the target generation module in the molecule generation model.

7. The method of claim 6, wherein the determining target molecular difference information based on the to-be-optimized molecules, the optimizing target, and a target encoding module in the molecule generation model, comprises:

determining initial molecular difference information corresponding to the to-be-optimized molecules based on the target encoding module; and iteratively adjusting the initial molecular difference information based on the optimizing target to obtain the target molecular difference information.

8. An electronic device, comprising:

at least one processor; and a memory communicatively connected to the at least one processor; wherein, the memory stores instructions executable by the at least one processor, and the instructions, when executed by the at least one processor, cause the at least one processor to perform operations for training a model, the operations comprising:

obtaining first molecular samples and second molecular samples;

determining molecular difference information based on the first molecular samples and the second molecular samples;

training an initial encoding module and an initial generation module based on the molecular difference information to obtain a target encoding module and a target generation module; and determining a molecule generation model based on the target encoding module and the target generation module, wherein the training an initial encoding module and an initial generation module based on the molecular difference information to obtain a target encoding module and a target generation module, comprises:

obtaining a preset difference training target;

training the initial encoding module based on the molecular difference information and the difference training target to obtain the target encoding module; and training the initial generation module based on the molecular difference information to obtain the target generation module.

9. The electronic device of claim 8, wherein the training the initial encoding module based on the molecular difference information and the difference training target to obtain the target encoding module, comprises:

determining a difference evaluation result corresponding to the molecular difference information based on the molecular difference information and the difference training target; and determining the initial encoding module as the target encoding module in response to determining that the difference evaluation result satisfies a preset difference condition.

10. The electronic device of claim 9, the operations further comprising:

in response to determining that the difference evaluation result fails to satisfy the difference condition, iteratively adjusting parameters of the initial encoding module to update the molecular difference information until an updated difference evaluation result satisfies the difference condition.

11. The electronic device of claim 8, wherein the training the initial generation module based on the molecular difference information to obtain the target generation module, comprises:

obtaining the molecular difference information;

determining updated information of the molecular difference information in a process of training the initial encoding module;

determining third molecular samples output by the initial generation module based on the first molecular samples, the molecular difference information, and the updated information; and training the initial generation module based on the third molecular samples and the second molecular samples to obtain the target generation module.

12. The electronic device of claim 8, wherein the determining molecular difference information based on the first molecular samples and the second molecular samples, comprises:

determining the molecular difference information based on the first molecular samples, the second molecular samples, and the initial encoding module.

* * * * *